(12) United States Patent
Ringermacher et al.

(10) Patent No.: US 7,805,251 B2
(45) Date of Patent: Sep. 28, 2010

(54) TWO SLOPE REFERENCE FOR SYNTHETIC THERMAL TIME OF FLIGHT IMAGING

(75) Inventors: Harry Israel Ringermacher, Delanson, NY (US); Donald Robert Howard, Troy, NY (US); Bryon Edward Knight, Charlton, NY (US); William George Patterson, Wilmington, DE (US)

(73) Assignee: General Electric Company, Niskayuna, NY (US)

( * ) Notice: Subject to any disclaimer, the term of this patent is extended or adjusted under 35 U.S.C. 154(b) by 179 days.

(21) Appl. No.: 12/246,896

(22) Filed: Oct. 7, 2008

(65) Prior Publication Data

US 2010/0088041 A1    Apr. 8, 2010

(51) Int. Cl.
*G06F 19/00* (2006.01)

(52) U.S. Cl. .................................................. 702/14
(58) Field of Classification Search .................. 702/40
See application file for complete search history.

(56) References Cited

U.S. PATENT DOCUMENTS

| 5,582,485 A | 12/1996 | Lesniak |
| 5,631,465 A | 5/1997 | Shepard |
| 5,683,181 A | 11/1997 | Shepard |
| 2002/0196184 A1* | 12/2002 | Johnson et al. ............. 342/387 |

* cited by examiner

*Primary Examiner*—Tung S Lau
(74) *Attorney, Agent, or Firm*—Penny A. Clarke

(57) ABSTRACT

A method including receiving a first line and a second line to be joined at a junction location to provide a reference curve. A corresponding system and computer program product.

12 Claims, 12 Drawing Sheets

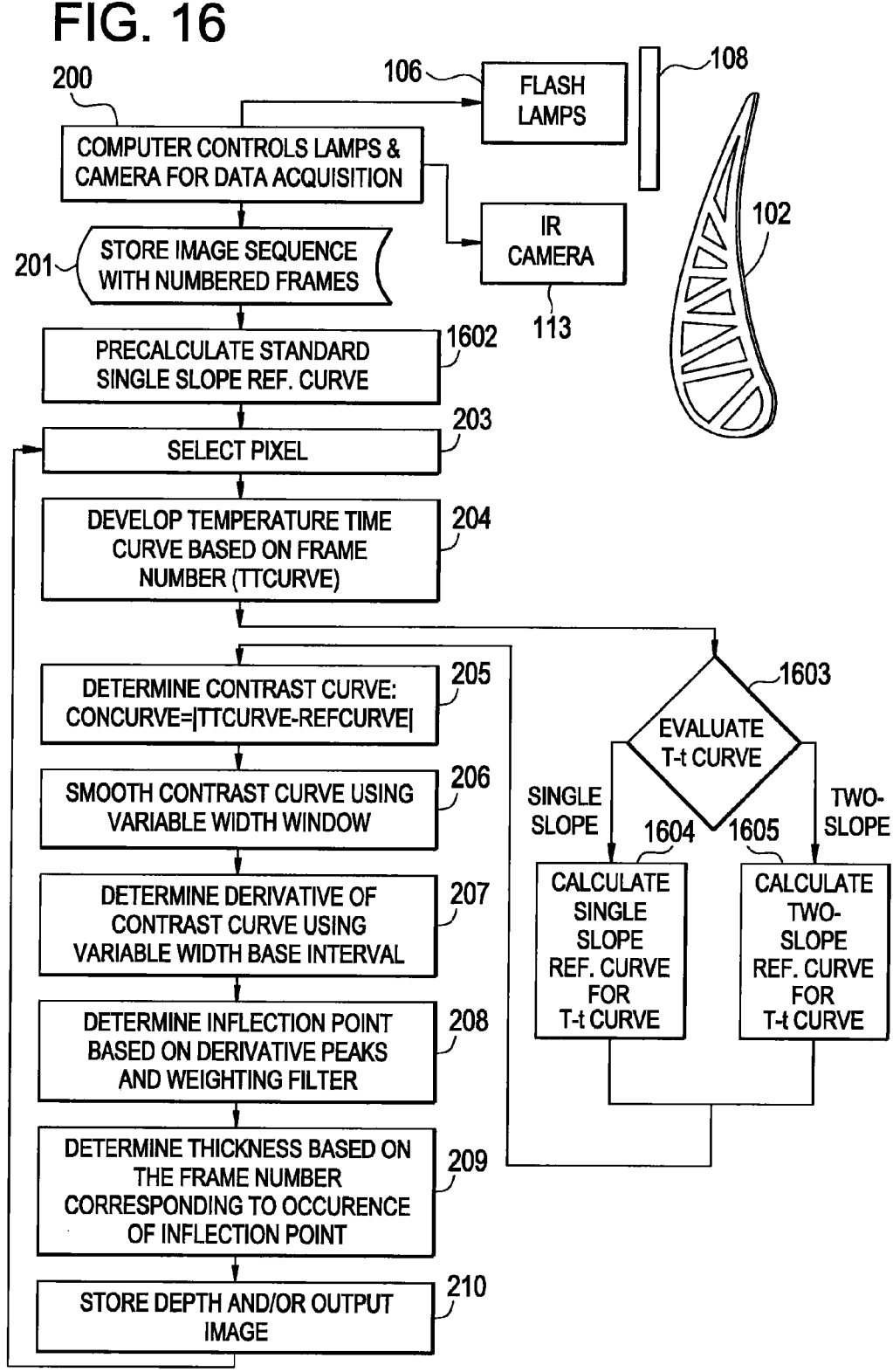

TWO SLOPE REFERENCE FOR SYNTHETIC THERMAL TIME OF FLIGHT IMAGING

BACKGROUND

Embodiments of the invention relate generally to thermal imaging for deep flaw detection in anisotropic media, and more particularly to two slope reference for synthetic thermal time of flight imaging.

Adjustment of temperature-time (T-t) reference curves, used in thermal imaging, for adaptation to deep flaw detection in anisotropic media is desirable. In such media, the ingoing thermal pulse follows 1-D heat flow while the pulse returning from the flaw to the surface follows 2-D flow since the flaw is typically closer to a point source. Log-log forms of the T-t curves have been used in practice since for 1-D flow they are straight lines of slope $-\frac{1}{2}$. Adjustment of the trailing end of the slope can improve the sensitivity to deep flaw imaging. Therefore, joining two lines of variable slope at an adjustable point in time so that its slope is continuous at the junction is desirable.

BRIEF DESCRIPTION

A Two slope reference for synthetic thermal time of flight imaging includes, in an exemplary embodiment, receiving a first line and a second line to be joined at a junction location to provide a reference curve. Another exemplary embodiment includes a corresponding system. Another exemplary embodiment includes a corresponding computer program product.

BRIEF DESCRIPTION OF THE DRAWINGS

These and other features, aspects, and advantages will become better understood when the following detailed description is read with reference to the accompanying drawings in which like characters represent like parts throughout the drawings, wherein:

FIG. 16 is a flowchart illustrating a process of infrared image data acquisition and analysis that includes a two slope reference curve calculation option as performed by the system of FIG. 1 in accordance with exemplary embodiments of the invention.

DETAILED DESCRIPTION

Figure 1:
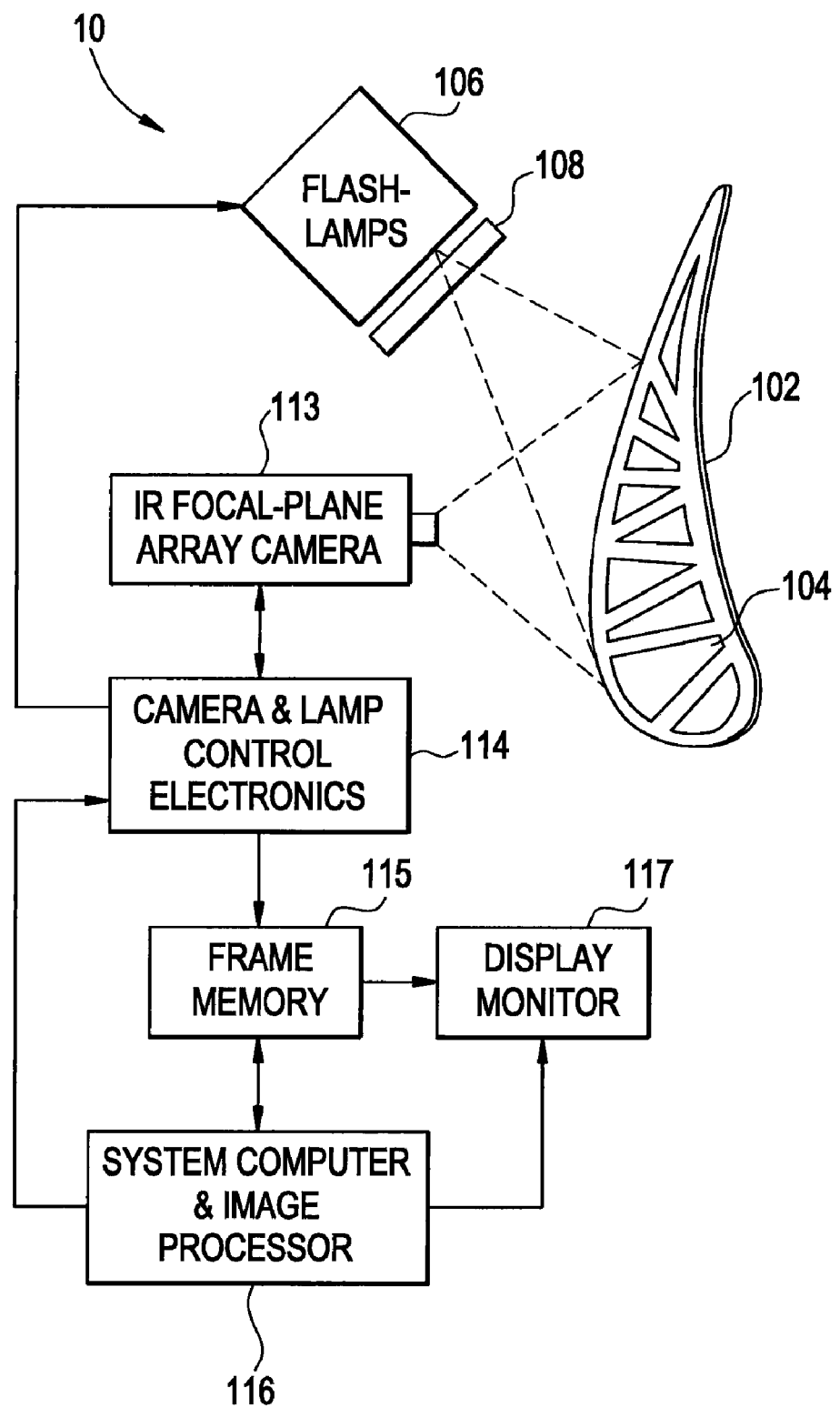
FIG. 1 is schematic diagram illustrating an example infrared transient thermography system arrangement for determining and displaying the actual thickness of an object in accordance with exemplary embodiments of the invention.

In the following detailed description, numerous specific details are set forth in order to provide a thorough understanding of various embodiments. However, the embodiments may be practiced without these specific details. In other instances, well known methods, procedures, and components have not been described in detail.

Further, various operations may be described as multiple discrete steps performed in a manner that is helpful for understanding embodiments of the present invention. However, the order of description should not be construed as to imply that these operations need be performed in the order they are presented, or that they are even order dependent. Moreover, repeated usage of the phrase "in an embodiment" does not necessarily refer to the same embodiment, although it may. Lastly, the terms "comprising," "including," "having," and the like, as used in the present application, are intended to be synonymous unless otherwise indicated.

Exemplary embodiments of the invention provide for adjustment of temperature-time (T-t) reference curves, used in thermal imaging, for adaptation to deep flaw detection in anisotropic media. In that regard, two lines of variable slope can be joined at an adjustable point in time so that the slope is continuous at the junction. Furthermore, exemplary embodiments of the invention relate to a nondestructive testing method and apparatus for determining and displaying the actual thickness of an object through the use of high speed infrared (IR) transient thermography. An improved high-speed IR transient thermography analysis approach is utilized to accurately measure the thickness of an object and provide a visual coded display indicative of its cross-sectional thickness over a desired area of the object. A salient feature of the present invention is that a "synthetic" or computed reference, based on actual surface temperature, is used to compute the contrast versus time data needed to determine thickness. As a result, at least one beneficial aspect of exemplary embodiments of the invention is that is does not require the use of a separate reference standard or a reference region on the examined object. In addition, when using the transient thermographic technique of exemplary embodiments of the invention there is no need to apply special coatings to the object(s) being examined. Moreover, exemplary embodiments of the invention can readily accommodate objects having non-uniform surfaces or varying surface emissivity.

Exemplary embodiments of the invention makes use of an inflection point in a temperature-time (T-t) response analysis of the surface of a rapidly heated object, preferably obtained from "front-side" IR camera observations. This inflection point, $t_{infl}$, occurs relatively early in the T-t response and is essentially independent of lateral heat loss mechanisms. Such considerations may be of particular relevance, for example, when working with metals since, due to the high thermal conductivity of metals, the thermal response of a metal object is fairly quick and, as a result, the time available for obtaining thermal data measurements is usually short. The inflection point, $t_{infl}$, is extracted from thermal data acquired over a predetermined time period from successive IR camera image frames. Preferably, this time period is at least somewhat longer than an anticipated characteristic time, as obtained from Equ.(1) (below), based on an estimation of the thickness of the object being evaluated.

$$T_C = 4L^2/\pi^2\alpha \qquad \text{Equ.(1)}$$

In accordance with exemplary embodiments of the invention, the inflection point, $t_{infl}$, is determined by utilizing pixel contrast data that is based on a "synthetic" or computed thermal reference instead of a "real" reference such as a slab standard or a suitable region on the examined object. This computed synthetic reference represents the surface temperature of an object as a function of time for one-dimensional heat flow into a semi-infinite medium (half-space) and is given by the following relationship:

$$T_s(t) = A[t^{1/2} - (t-\tau)^{1/2}] \qquad \text{Equ.(3)}$$

where $T_s(t)$ is the surface temperature of the synthetic thermal reference as a function of time t, A is a parameter selected to match actual surface temperature on an object surface at a location corresponding to a selected analysis pixel in an acquired IR image, and τ is a duration of heating the object before acquiring image frames.

The reference temperature-time data provided by Equ. (3) describes a "synthetic" half-space thermal decay based on an initial temperature, A, at a particular location on the surface of the object. As described in greater detail below, the "synthetic" thermal reference data as obtained from Equ. (3) is first computed for each (x,y) pixel location of the imaged object and then used to determine contrast as a function of time for each pixel. Moreover, as a further advantage, determination of the synthetic thermal reference data is not dependent upon the nature or characteristic of the particular material or metal being evaluated since it is not a parameter in Equ. (3).

As illustrated in FIG. 1, an apparatus according to exemplary embodiments of the invention includes an imaging system 10 comprising one or more high power flash lamps 106 fitted with special optical filters 108, an IR sensitive focal-plane array camera 113 for data acquisition and a display monitor 117. A computer system 116 controls the imaging system 10, records and analyzes surface temperature data acquired via the IR camera 113 and provides a color or gray pattern-keyed image on the display monitor 117 that accurately corresponds to thickness of the object 102.

The acquisition of surface temperature data is initiated by firing the flash-lamps 106 to illuminate the surface of the object 102. The special optical filters 108 are spectrally tuned to absorb and/or reflect all 3-5 micron IR radiation back into the flash-lamp(s). This prevents undesirable long-wave IR "afterglow" emissions (typically generated by overheated metallic elements in the flash-lamps 106 after the lamps 106 are extinguished) from reaching the object 102 or the camera 113. The use of such filters 108 enables a more precise thermal evaluation that can produce dimensional measurements within an accuracy range of 1%-3% of actual thickness.

A predetermined number of image frames are then recorded over a period of time after the flash lamps 106 are fired and the recorded images used to develop a temperature-time (T-t) history for every elemental region or "resolution element" over the region of interest on the object surface. Each recorded image frame is comprised of a predetermined n×m array of image pixels whose intensity correlate to the surface temperature of the object 102 at the time the frame data was acquired, each pixel having an (x,y) location designation within the image frame that corresponds to a particular resolution element.

A heat flow analysis of the T-t history is then conducted for each pixel in the acquired image frames to determine the thickness of the object at each resolution element location. Analysis of transient heat flow through solid portions of an object includes determining a characteristic time, $T_c$, needed for a "pulse" of thermal energy to penetrate the object at a first surface, reflect off an opposite surface and return to the first surface. Since this characteristic time is related to the distance between the two surfaces, it can be used to determine the thickness of the object between the two surfaces at a desired point. Because $T_c$ is also related in time to the occurrence of an inflection point, $t_{infl}$, in the contrast-versus-time data history of a pixel according to Equ. (2) (shown below) above, a value for characteristic time $T_c$ may be determined by using a recorded intensity-versus-time history of the pixel to compute contrast-versus-time data for the pixel, which in exemplary embodiments of the invention is accomplished by subtracting the "synthetic" thermal reference T-t data from the recorded intensity-versus-time data of the pixel.

$$t_{infl} = 0.9055 T_c \qquad \text{Equ.(2)}$$

Using the synthetic thermal reference, a contrast-versus-time curve is determined for each (x,y) pixel location corresponding to each resolution element of the object surface. Next, Gaussian temporal smoothing of the pixel contrast curve data is employed to improve the signal-to-noise ratio of the measurements. The mathematical derivative of the contrast curve is then computed to identify an inflection point in the data. This derivative may be computed using a three-point data sampling having a first and third sample point separation that is proportionally related to the value of the image frame number at the second sample point. Next, all local "peaks" in the contrast curve obtained from the derivative computation are identified and a weighting function is used as a filter to adjust the significance of localized each of these peaks to identify the actual inflection point in the T-t contrast curve data for use in determining object thickness. Finally, thickness of the object at a location corresponding to each pixel is quantitatively determined according to Equ. (1) and Equ. (2) above.

As introduced above, FIG. 1 illustrates an example infrared (IR) transient thermography system 10 for determining and displaying the thickness of an object 102, e.g., a metal turbine airfoil 102 having intentional voids 104. For the purposes of the following discussion, the "thickness" of an object refers to a front wall or surface thickness in the context of a hollow or semi-hollow object (i.e., an object having an intentional void).

As shown in FIG. 1, a flash-lamp heat-pulse source 106 is used to rapidly heat the surface of the object being measured. One suitable arrangement for flash-lamp heat-pulse source 106 would be, for example, a set of four or eight high-speed, high output power photographic flash-lamps, each capable of about 4.8 Kilo-joules output and having individual power supplies.

Since metals have a significantly faster rate of heat conduction than non-metals, the characteristic times for heat flow in metals are much faster than those of, for example, plastic or composite materials. Consequently, in attempting to adapt conventional IR thermography techniques (ordinarily limited to non-metals) to metals, a sharp cutoff in the applied heat is needed. In order to obtain this, a 3-5 micron reflective filter 108 is used between (covering) flash-lamps 106 and object of interest 102 so as to prevent exposing the object to residual heat as the flash-lamps 106 cool down after exposure.

In practice, one or more filters may be used (e.g., one per each flash-lamp). These filters act to prevent direct long wave radiation typically generated from the "afterglow" of overheated metallic elements in the flash-lamps 106 from ever leaving the flash-lamps and impinging on the target or otherwise reflecting back into focal-plane array camera 113. Such primary afterglow radiation from flash-lamps 106 competes and can interfere with the long-wave IR emissions from the targeted object during early thermal data acquisition, thus obscuring the true target-generated IR radiation and reducing ultimate image contrast and quality. Thus, the use of these special filters produces a sufficiently sharp heat pulse to enable the shorter heat travel time in metal to be detected.

In the example embodiment depicted in FIG. 1, flash-lamp filter 108 may be composed of Pyrex®, fused quartz, BK7™, or other optical material that is transparent to visible and UV light and is coated on the flash-lamp facing side with an infrared-reflective coating to reflect all radiation in the 3-5 micron range back into the flash-lamps. (Optical glass and coated filters may be acquired or specially manufactured by a general scientific optics and optical glass manufacturer).

Surface temperature measurements of heat-pulse illuminated object 102 are acquired using an IR sensitive imaging system comprising an IR sensitive focal-plane array camera 113, control electronics 114, frame data memory 115, control computer/image processor 116 and display monitor 117. Acquisition of thermal data is typically initiated at the time of flash lamp firing either by optical triggering or by other suitable means. Flash-lamp firing is controlled via flash-lamp electronics 114 managed by video frame acquisition software running on system computer 116.

The system control computer/image processor 116 may be a specially programmed general purpose digital computer that is capable of peripheral equipment control and communication functions in addition to digital image processing and display in accordance with exemplary embodiments of the invention. System computer 116 controls camera and lamp electronics 114 and frame data memory 115 to acquire a predetermined number of successive thermal image frames of the object surface which are stored in memory 115 for future analysis.

Before beginning the thermal imaging process, IR camera 113 is first calibrated using a "full-field" dual-image calibration technique as now described. This technique employs two "black-body" (BB) image calibration references: a BB "cold" source using a room-temperature flat-black plate and a BB "hot" source using a heated flat-black plate. For example, for acquiring the BB "cold" source calibration image, a flat-black painted box enclosing the room-temperature flat-black plate, arranged at a 45 degree angle to the camera lens, is placed directly in front of the lens. For acquiring the BB "hot" source calibration image, the camera lens is placed into the same flat-black painted box unit after heating the flat-black plate (nominally to about 10 degrees C. above ambient) such that the camera images the heated plate over its full field. The above described dual-image calibration technique is exemplary and any other calibration technique that results in producing maximum uniformity of the image field (i.e., for high contrast imaging and obtaining improved thermal accuracy) can be used.

Each image frame acquired during the imaging process consists of N×N pixels (each pixel corresponding to a resolution element on the object surface), where N is typically either 128 or 256 depending on the resolution and accuracy desired. Each pixel occupies about two bytes of storage memory and may be represented, for example, by a 12-bit or larger binary number. The stored image frames are sequentially identified with increasing frame number values that together serve to provide a historical record of the temperature versus time (T-t) characteristics of a front surface of object 102 for a predetermined period after being struck by the heat impulse imparted by flash-lamp 106.

During evaluation of a metal object 102, after control computer 116 triggers the firing of flash-lamp(s) 106, image data frames are acquired from camera 113 and the IR intensity at each resolution element on the image is digitally recorded and stored in frame data recorder 115. Data acquisition continues over a predetermined number of sequential image frames that are sufficient to acquire a meaningful T-t history over a duration of at least one estimated "characteristic time" for the material of the object 102. The total number of image frames acquired may vary depending on the accuracy and image resolution desired and can be as high as 550 frames per second of data acquisition.

Frame data recorder 115 may be a conventional digital memory internal to processor 116 or any suitable video frame data storage device accessible by processor 116. Each successive thermal image frame acquired is assigned an increasing frame number, Z, corresponding to the passage of real time. The resulting data frame "stack" is then analyzed taking a one-dimensional heat flow analysis approach, as outlined above. In accordance with this approach, exemplary embodiments of the invention take advantage of a known thermal invariance property, evidenced in the temperature vs. time (T-t) history of each image pixel over successive IR image frames that relies on identifying the location of an "inflection point" or peak-slope time, i.e., the point in time of maximum slope on the T-t data curve.

Figure 2:
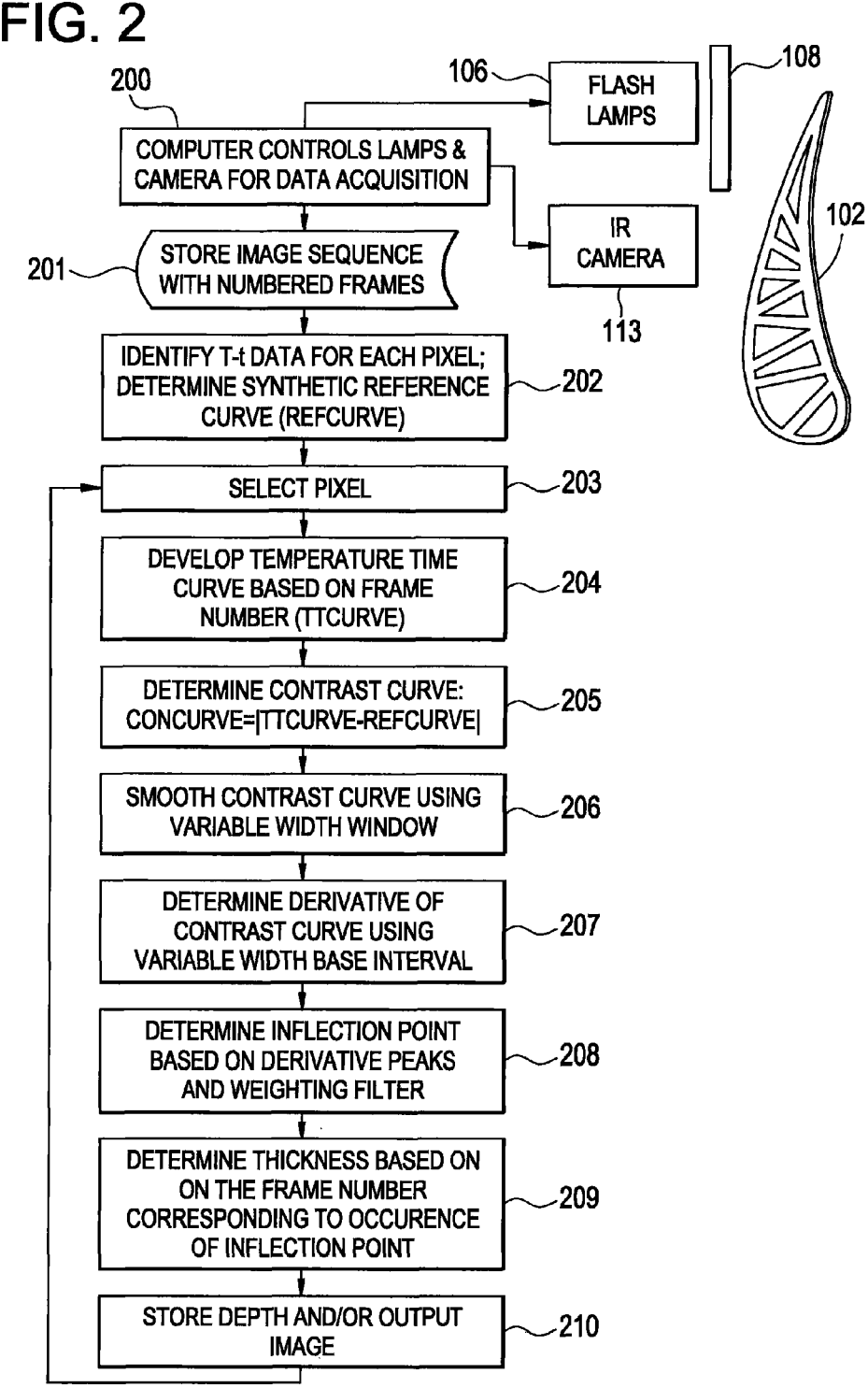
FIG. 2 is a flowchart illustrating a process of infrared image data acquisition and analysis as performed by the system of FIG. 1 in accordance with exemplary embodiments of the invention.

Referring now to FIG. 2, a flow diagram is presented that illustrates example processing steps for conducting transient IR thermography using synthetic-reference thermal imaging techniques of exemplary embodiments of the invention. These steps may be implemented, for example, by appropriately programming computer 116 (FIG. 1) using known conventional programming techniques.

Initially, as indicated at block 200, a region of interest on the object 102 is identified (i.e., the IR camera 113 is focused to capture the region of interest) and the system operator selects or inputs information concerning relevant parameters for examining the object 102 such as, for example, a thermal diffusivity coefficient for the material 102. Next, as indicated at block 200 in FIG. 2, the system control computer instructs the flash-lamp electronics to fire flash-lamps 106 and initiate image frame data acquisition from the focal plane array IR camera 113. Data acquisition proceeds over a predetermined number of sequential image frames and then, as indicated at block 201, the image sequence is stored in frame memory 115 after identifying each acquired image frame with a sequential frame number, Z.

Next, as indicated at block 202, a set of T-t curve data is identified for each pixel in the thermal image corresponding to each resolution element location over the region of interest on the surface of the object 102. Also, a time and frame number of the initial IR "flash" heating is identified, a first unsaturated data frame is identified, and a "synthetic" half-space thermal decay T-t reference data curve (refcurve) is generated based upon an initial surface temperature parameter, A, and the flash duration, τ, according to Equ (3) as given above.

Equ. (3) is valid for times (t) greater than or equal to τ (the flash heating duration). Preferably, the parameter A is chosen to match the actual initial value of temperature as measured at a selected analysis pixel in the image. With this approach, the starting temperature for a synthetic thermal decay reference, thus generated, is rendered adjustable at each pixel without having to know the nature of the particular material being examined. Thus, if different pixels have varying starting temperatures, the generated synthetic reference of exemplary embodiments of the invention can accommodate such variations; whereas, a "real" slab standard thermal reference can not, since it is limited to a fixed-value starting temperature.

As indicated at blocks 203 and 204, a first pixel (or the next pixel) is then selected for analysis and its T-t curve data (ttcurve) is developed from recorded pixel intensity data stored in frame memory 115. At this point, optional offset and scale (amplitude) adjustments can also be made to help compensate for any derogatory effects such as, for example, loss of amplitude due to surface curvatures. Next, as indicated at block 205, a contrast curve (concurve) is determined for the selected pixel by subtracting the synthetic reference T-t curve data (refcurve) from the T-t curve (ttcurve) data of the pixel.

As indicated at block 206, a Gaussian function temporal smoothing of the contrast curve data may also be performed. In a preferred embodiment, a "temporal window" used in the Gaussian smoothing algorithm is made to vary as a function of time by making it proportional to the image frame number, Z, corresponding to the contrast data. This smoothing "window" controls the full-width of the Gaussian at half-maximum (i.e., the "2-.σ" width). Using a variable-width frame-number smoothing as described is more advantageous than a traditional Gaussian smoothing because it tends to compensate for the effects of heat diffusion at increasing depths within the material. Preferably, for this step, the width of the smoothing window at a selected data point is made proportional to the square-root of the image frame number at that point. In addition to the described variable-width frame-number Gaussian temporal smoothing, a number of software implemented "imaging filters" may also be applied to the contrast curve data at this stage, including spatial smoothing, initial and ending noise suppression, negative contrast suppression and contrast thresholding.

Next, at block 207, the mathematical derivative of the contrast curve, indicative of the inflection point, is determined As is known, the point of maximum slope on a curve can be determined by using a conventional 3-consecutive-point derivative algorithm in which three equally spaced consecutive data points along the curve are sampled and used to calculate the slope of the curve at the second (middle) data point. In accordance with exemplary embodiments of the invention, three points are still used to determine the derivative of the contrast curve, but the separation of the first and third sample derivative points (i.e., the width of the derivative base interval) is linked to real time in the image evolution via the image frame number. Specifically, the width of the derivative base interval at any selected point along the contrast curve is made proportional to the square-root of the IR image frame number, Z.

In this manner, the signal-to-noise (S/N) characteristics are maximized even in the midst of high noise levels. This improvement in the S/N ratio results from "sampling" over a larger interval and, thus, detects the largest signal change rather than the differential change traditionally obtained with fixed-width 3-point differentiation. Since a maximum S/N ratio is obtained when the sample point separation is equal to the full Gaussian width, a maximum S/N ratio is consistently achieved by using the frame-number proportional-width approach of exemplary embodiments of the invention.

Next, at block 208, all local peaks in the derivative curve are identified and a significance "weighting" factor is used to assess the proper peak to use as the $t_{infl}$ inflection point. During this block, a list of all peak location times (i.e., frame numbers) and amplitudes is maintained in computer memory. By applying a predetermined appropriate weighting function to the peak list, it is possible to adjust the significance of each peak so that, for example, peak-producing noise effects arising early in the data acquisition time are effectively discounted. Since empirical evidence indicates that peaks occurring later in time tend to be more significant, a temporal weighting function is implemented in the present example embodiment by simply multiplying the amplitude of a peak by the time at which it occurred. The peaks are then sorted according to decreasing significance (weight) and the peak having the greatest weighting value (i.e., the most significant) is selected as indicative of the proper inflection point.

Next, at block 209, the thickness of the object 102 at the location of the resolution element corresponding to the selected pixel is determined. This is accomplished by identifying the frame number in which the most significant peak occurs, i.e., the inflection point $t_{infl}$, and converting that value to real time. Since acquisition of IR image frames occurs at a fixed predetermined rate, a frame number can be equated to a real elapsed time. Accordingly, the frame number of the IR image frame harboring the most significant peak in the derivative curve provides an actual quantitative time value for t.sub.infl. Using this value for $t_{infl}$ in Equ. (1) and Equ. (2) (above), provides a thickness value, L, denoting the actual thickness of the object 102 at the location of the resolution element corresponding to the analyzed pixel.

Next, at block 210, the thickness value, L, is stored in memory and used to build a color-mapped or gray-scale image of the region of interest on the object surface for display or print, each color or gray shade corresponding to a particular thickness. The next pixel is then selected, as indicated at block 203, and the above blocks are reiterated for each pixel comprising the IR image.

In addition to the steps outlined above, the input and selection of various parameter values such as diffusivity constant, data analysis starting point and range, temporal smoothing window size range, and color mapping range are automated for accuracy and consistency through, e.g., appropriate conventional programming of the system control computer 116.

By conducting the transient thermography analysis using the above described steps for thermal data acquisition and analysis in conjunction with the above described apparatus in accordance with exemplary embodiments of the invention, wall thickness values can be accurately obtained even between closely spaced back wall or internal structures that may form a part of, or be connected to, the tested object (e.g., the rib-like structures often found in turbine air foils, as depicted e.g. in FIG. 1), whereas using traditional thermal or ultrasonic methods such closely positioned back-wall structures would normally result in blurred images and distorted data.

Figure 3:
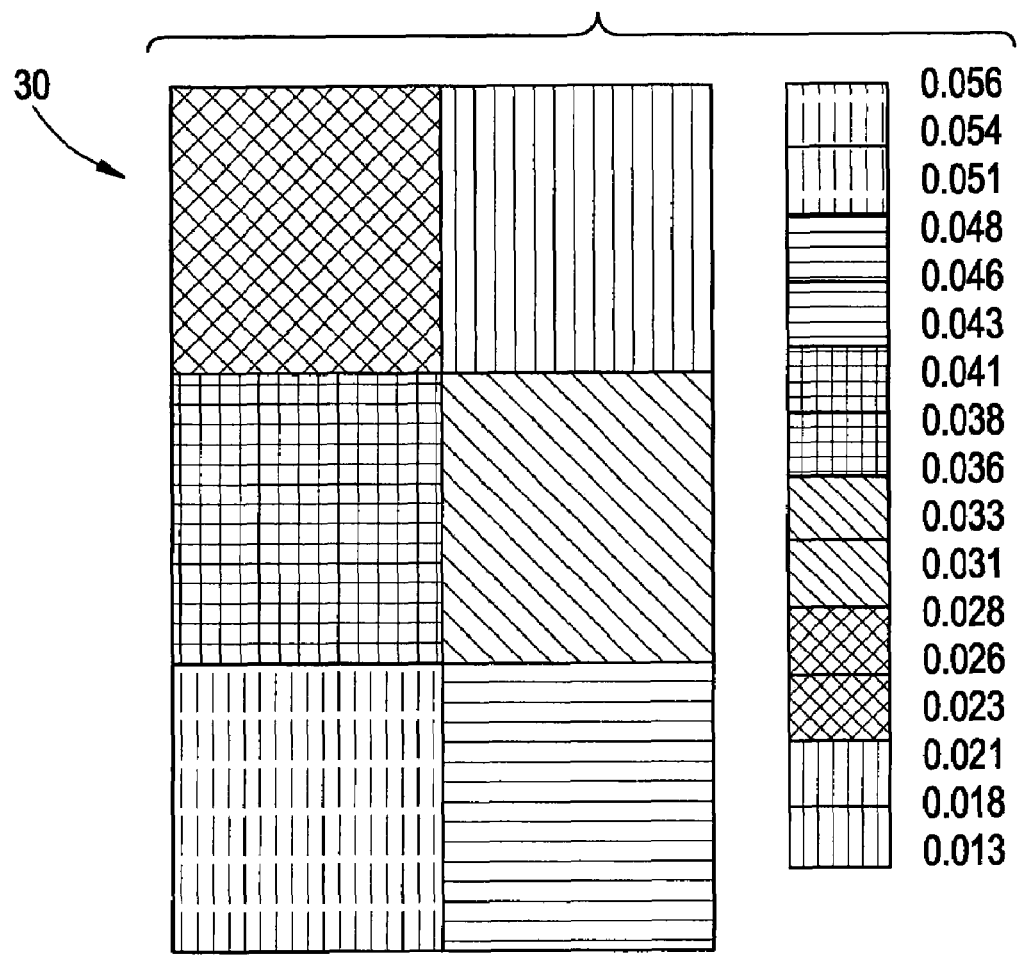
FIG. 3 is an example print of an infrared transient thermography image display of a nickel-alloy metal step-standard in accordance with exemplary embodiments of the invention.

In FIG. 3, a diagram of an infrared transient thermography display image for a multi-tiered object block is depicted. Object block 30 depicted in FIG. 3 has six square sections of different thickness. The thickness of each of the six sections is indicated by a different color or gray tone in the generated image (shown here as different cross-hatch patterns) which corresponds to a like color or shade in a bar-scale thickness key displayed at the right of the image. In this example, the bar-scale includes indicia of thickness ranging from 0.013 to 0.056 inches, but a displayed bar-scale having a different range may also be used.

Figure 4:
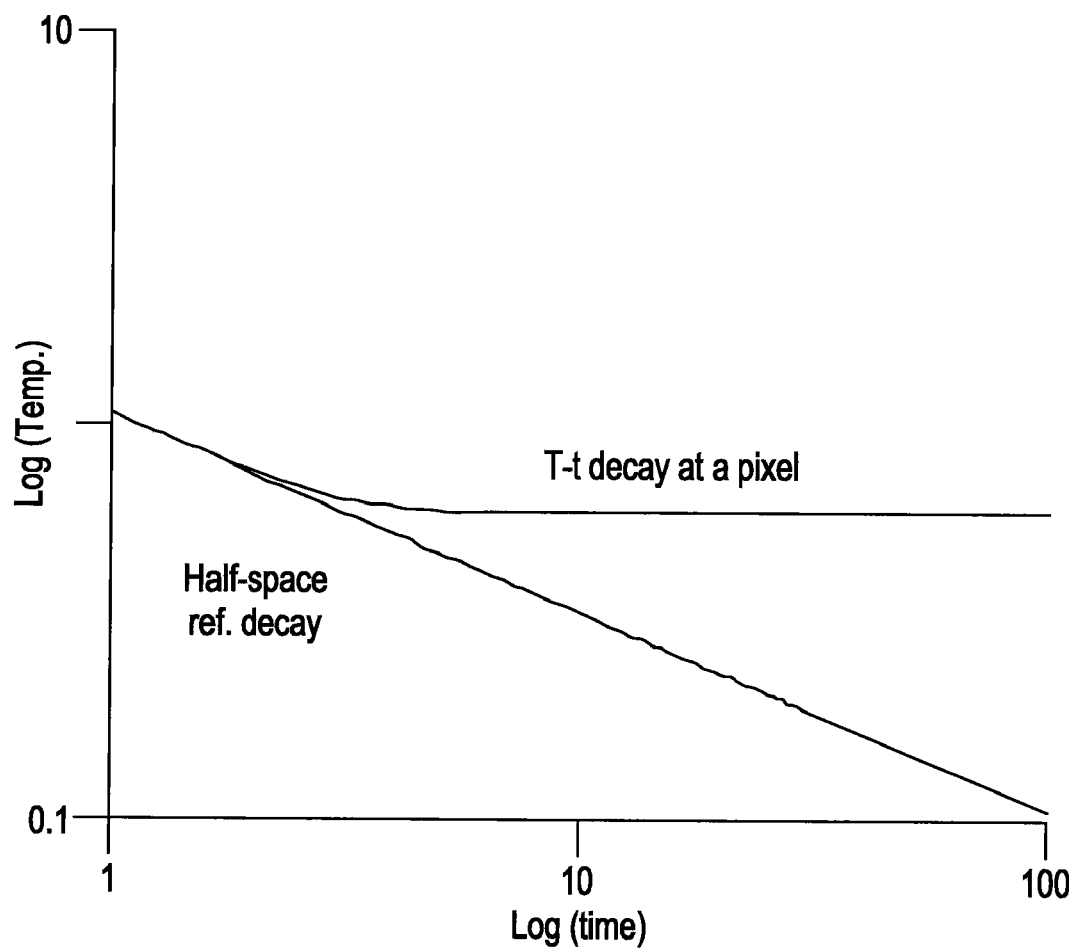
FIG. 4 shows a "log-log" graph of a single-slope reference curve in accordance with exemplary embodiments of the invention.

FIG. 4 shows a "log-log" graph of a single-slope reference curve (referred to as a "Half-Space" curve), which is a standard response of a decay of heat from a surface into an infinitely deep substrate and falls off at the inverse square-root of time. The graph plots the logarithm of temperature against the logarithm of time and appears as a straight line in this format (lower curve). The upper curve is the T-t response of a heat decay into a plate of finite thickness. These two curves, when plotted in a normal graph, are subtracted to produce the "contrast" needed to create the depth image described above.

The following are "Ringermacher Splicing Functions" for joining two curves in accordance with exemplary embodiments of the invention:

$$W_2(x) = \frac{1}{1+e^{\frac{(x-x_0)\log 10}{w}}}$$

$$W_1(x) = \frac{1}{1+e^{\frac{(x_0-x)\log 10}{w}}} \quad \text{Equ. (4)}$$

Figure 5:
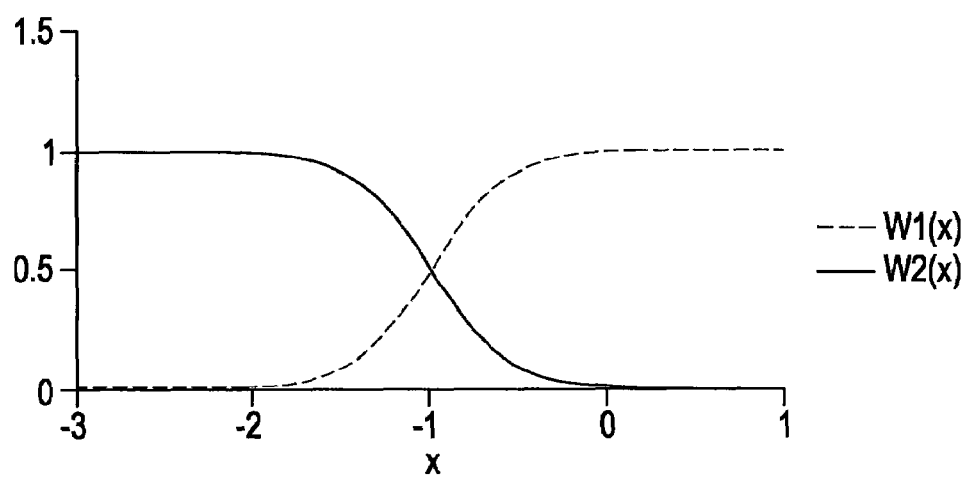
FIG. 5 shows an example of "Ringermacher splicing functions" for joining two curves in accordance with exemplary embodiments of the invention.
Figure 6:
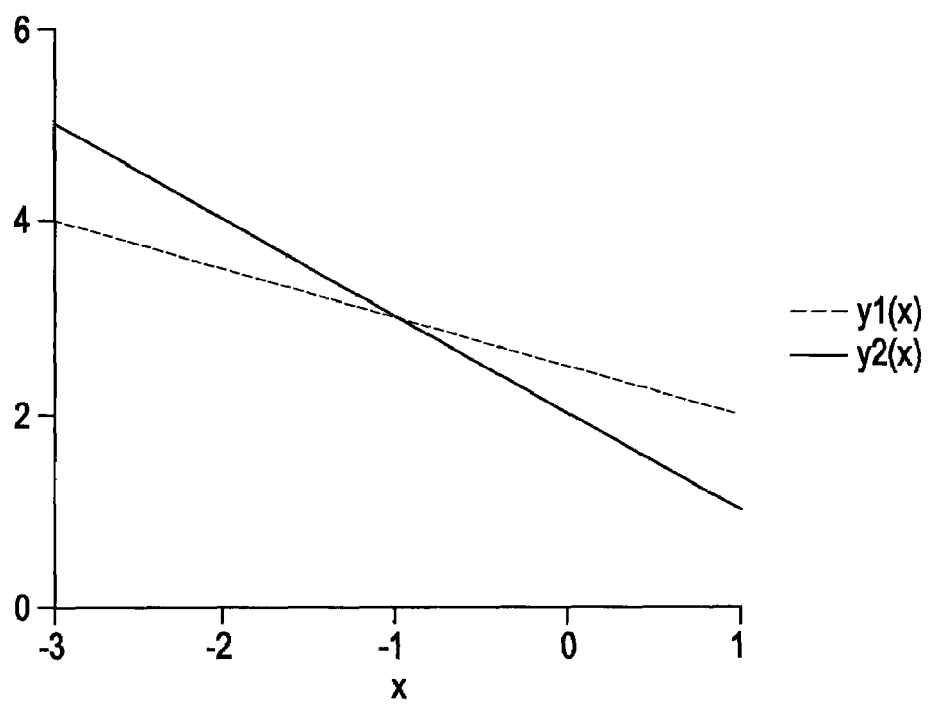
FIG. 6 shows lines of slope $m_1$ and $m_2$ intersecting at $x_0=-1$ in accordance with exemplary embodiments of the invention.

In Equ.(4), x is a variable location on the x-axis, $x_0$ is the fixed junction location and w is a "width" parameter controlling the junction sharpness. The behavior of $W_1$ and $W_2$ for $x_0=-1$ and w=0.4 is shown in FIG. 5. $W_1+W_2=1$ everywhere. $W_2$ is considered a weight (multiplying) function approaching unit amplitude for $x_0<-1$ and approaching zero amplitude for $x_0>-1$. $W_1$ is the converse. The limit of either as $w\to 0$ is known as the Heaviside unit step function.

In accordance with exemplary embodiments of the invention, two lines of slopes $m_1$ and $m_2$ are desired to be joined at a point $x_0$. The lines are shown in FIG. 5. One line segment to the left of $x_0$ is to remain intact along with the other segment to the right of $x_0$ and these line segments are desired to be joined at $x_0$ smoothly.

The two lines are described by:

$$y_1(x)=m_1 x+B_1 \quad y_2(x)=m_2 x+B_2 \quad \text{Equ.(5)}$$

The y-intercept of $y_1$ in Equ.(5) is $B_1$. The y-intercept of $y_2$ in Equ.(5) is $B_2$. The lines are desired to be joined at a point $x_0$ that can be adjusted. Therefore, in order to make a proper junction, $B_1$ and $B_2$ should be related by:

$$B_1=(m_2-m_1)x_0+B_2 \quad \text{Equ.(6)}$$

Figure 7:
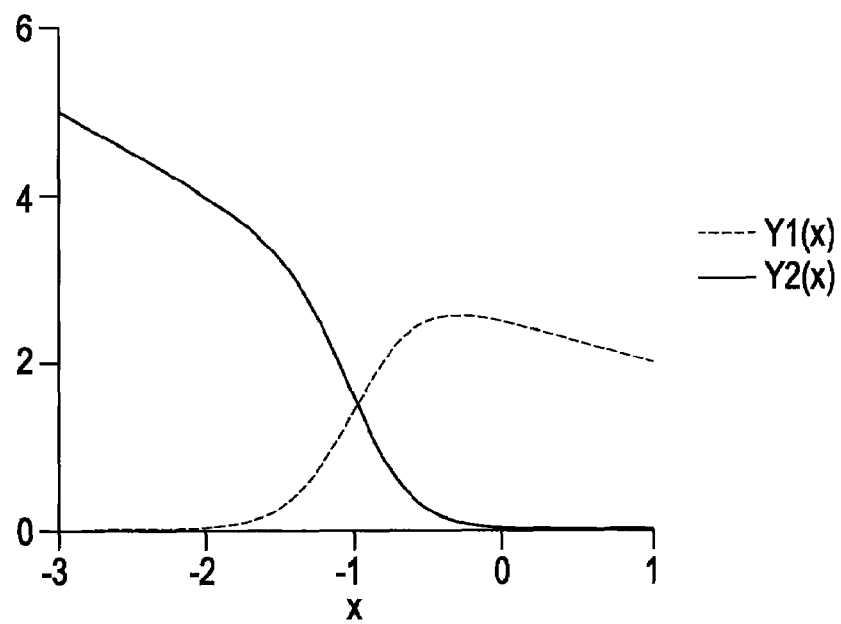
FIG. 7 shows the splicing functions shown in FIG. 5 applied to the lines shown in FIG. 6 in accordance with exemplary embodiments of the invention.

Then $B_1$ will self-adjust when $x_0$ is changed. Thus, when splicing function $W_2$ is applied to line $y_2$ (by multiplication) and splicing function $W_1$ is applied to line $y_1$, the result shown in FIG. 7 is obtained.

Figure 8:
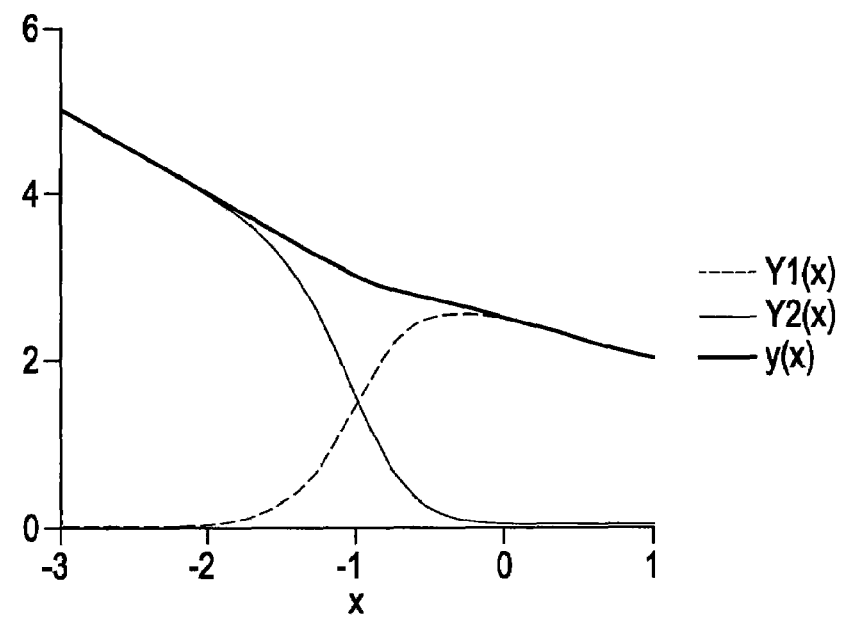
FIG. 8 shows the splicing functions shown in FIG. 5 applied to the lines shown in FIG. 6 and summed with a width parameter of 0.4 in accordance with exemplary embodiments of the invention.

The desired joined line (y(x)) shown in FIG. 8 is obtained by inserting the appropriate intercept, $B_1$, and applying the splicing functions (Eq.(4)) to the lines described by:

$$y(x)=Y_1(x)+Y_2(x) \quad Y_1(x)=W_1 y_1(x) \quad Y_2(x)=W_2 y_2(x) \quad \text{Equ.(7)}$$

Figure 9:
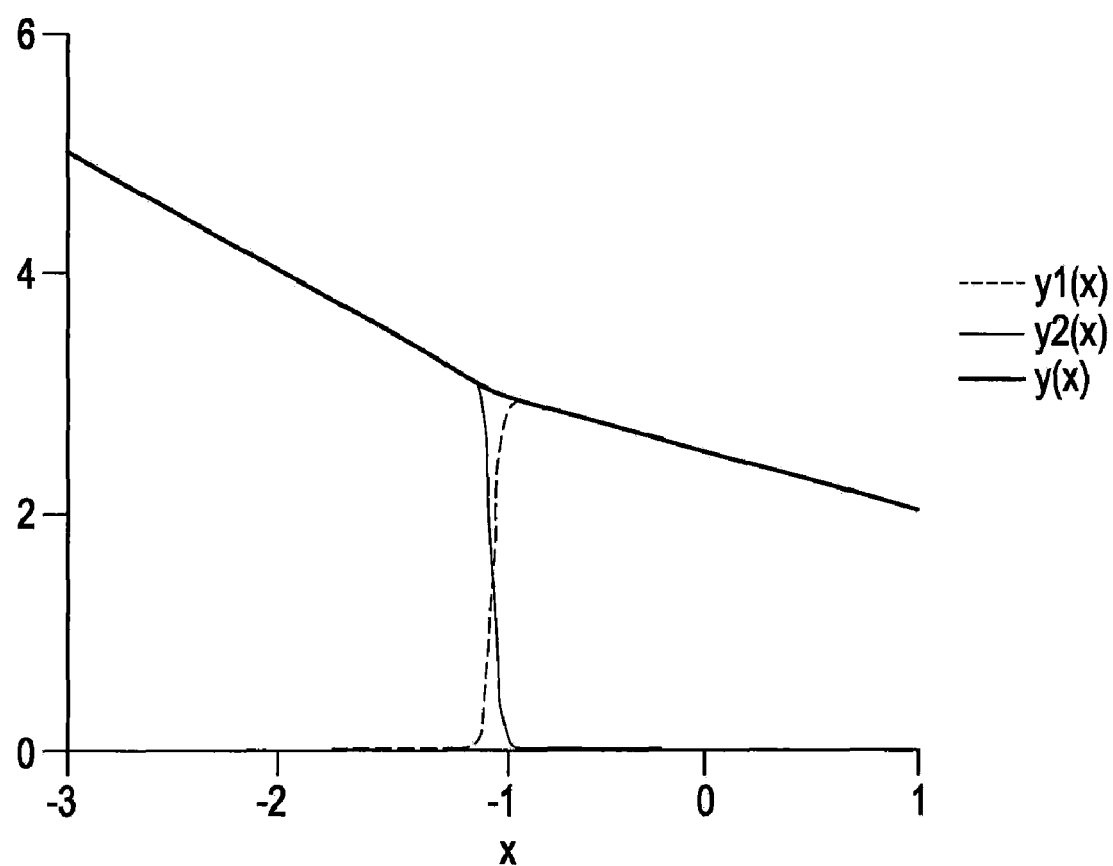
FIG. 9 shows the splicing functions shown in FIG. 5 applied to the lines shown in FIG. 6 and summed with a width parameter of 0.05 in accordance with exemplary embodiments of the invention.
Figure 10:
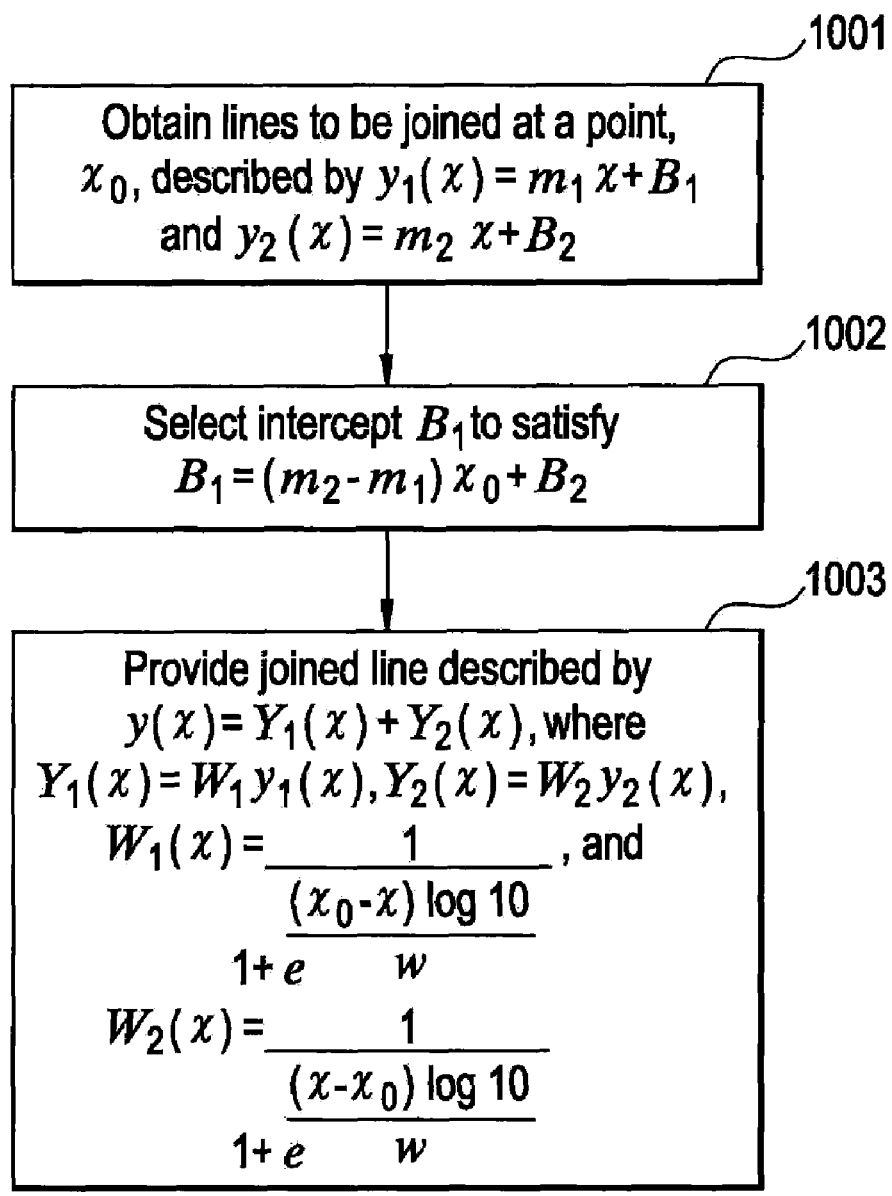
FIG. 10 is a flowchart illustrating a process of calculating a reference curve for a two slope line set as performed by the system of FIG. 1 in accordance with exemplary embodiments of the invention.

FIG. 9 shows the results of the same application as described above for a narrower width, w=0.05, which sharpens the junction. Both the junction point continuity and slope continuity are noted. As the junction point moves, the intercept will adjust. In general, this can be achieved with multiple segments in a similar way. FIG. 10 is a flowchart illustrating a process of calculating a reference curve for a two slope line set as performed by the system of FIG. 1 in accordance with exemplary embodiments of the invention. Blocks 1001, 1002, 1003 summarize the above described implementation with respect to FIGS. 5-9.

The following describes exemplary applications of the above described implementations to log-log plots in IR imaging. This formalism can be applied, e.g., to temperature-time curves in log-log graphs. In the following, log base 10 is assumed throughout. An ideal half-space temperature-time curve decays with time as $1/\sqrt{t}$. In log-log plots it is a straight line with constant slope $-\frac{1}{2}$. At times, some anisotropic materials deviate from this ideal behavior in the presence of flaws (i.e., 2-D heat flow). It is then desirable to create a "two slope" log-log function mimicking this behavior where the early slope may represent a 1-D half-space behavior while the later slope represents a changed 2-D behavior. The above implementation is translated as straight lines in log-log plots. Thus, y(x) is now temperature T(t), $B_1$ and $B_2$ are log(T) intercepts, x and $x_0$ are now log(t) quantities, and w is a given width on the log(t) axis. The following definitions are applied:

$$x=\log(t) \quad x_0=\log(t_0) \quad B_2=\log(T_2) \quad B_1=\log(T_1) \quad \text{Equ.(8)}$$

Carrying out the addition of the two lines in logarithmic form, using Equ.(5), (7), and (8), results in the following:

$$\log T(t)=W_1(t)[m_1 \log(t)+(m_2-m_1)\log(t_0)+\log(T_2)]+W_2(t)[m_2 \log(t)+\log(T_2)] \quad \text{Equ.(9)}$$

Exponentiating to get back to T-t space yields the following:

$$T(t)=10^{W_1(t)[m_1 \log(t)+(m_2-m_1)\log(t_0)+\log(T_2)]+W_2(t)[m_2 \log(t)+\log(T^{2)}]} \quad \text{Equ.(10)}$$

The result in Equ.(10) reduces to the following simpler form:

$$T(t)=T_2 t_0^{(m_2-m_1)W_1(t)} t^{m_1 W_1(t)+m_2 W_2(t)} \quad \text{Equ.(11)}$$

where $W_1$ and $W_2$ have been simplified by insertion of the log definitions of Equ.(8), as follows:

$$W_2(t) = \frac{1}{1+\left(\frac{t}{t_0}\right)^{\frac{1}{w}}} \quad \text{Equ. (12)}$$

$$W_1(t) = \frac{1}{1+\left(\frac{t_0}{t}\right)^{\frac{1}{w}}}$$

Equ.(11) together with Equ.(12), given $m_1$, $m_2$, $t_0$ and w, are the results of the 2-slope formalism in accordance with exemplary embodiments of the invention.

Figure 11:
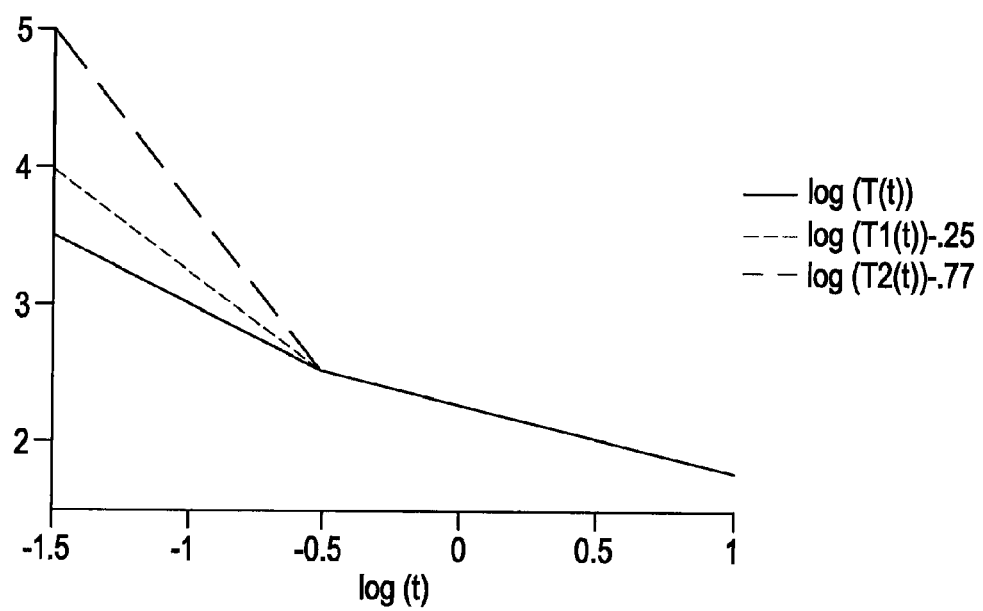
FIG. 11 shows the splicing functions shown in FIG. 5 applied to the lines shown in FIG. 6 for several slope selections $m_1$ with $m_2$ fixed in accordance with exemplary embodiments of the invention.
Figure 12:
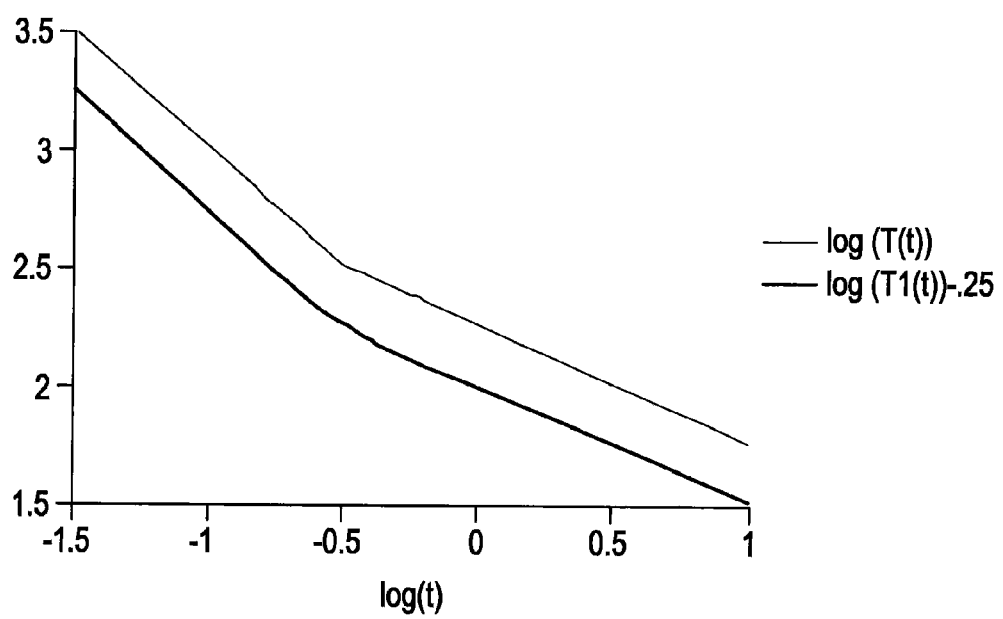
FIG. 12 shows the splicing functions shown in FIG. 5 applied to the lines shown in FIG. 6 for two width selections in accordance with exemplary embodiments of the invention.
Figure 13:
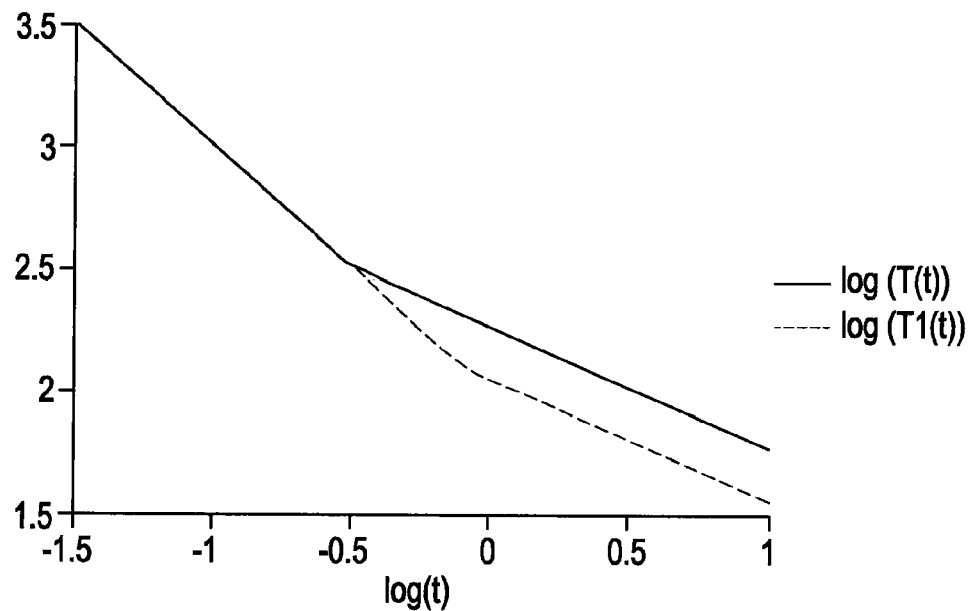
FIG. 13 shows the splicing functions shown in FIG. 5 applied to the lines shown in FIG. 6 for two junction locations in accordance with exemplary embodiments of the invention.

FIG. 11 shows the lines for several slope selections $m_1$ with $m_2$ fixed. FIG. 12 shows the joined lines for two width selections, w. FIG. 13 shows the joined lines for two junction locations, $x_0$.

Figure 14:
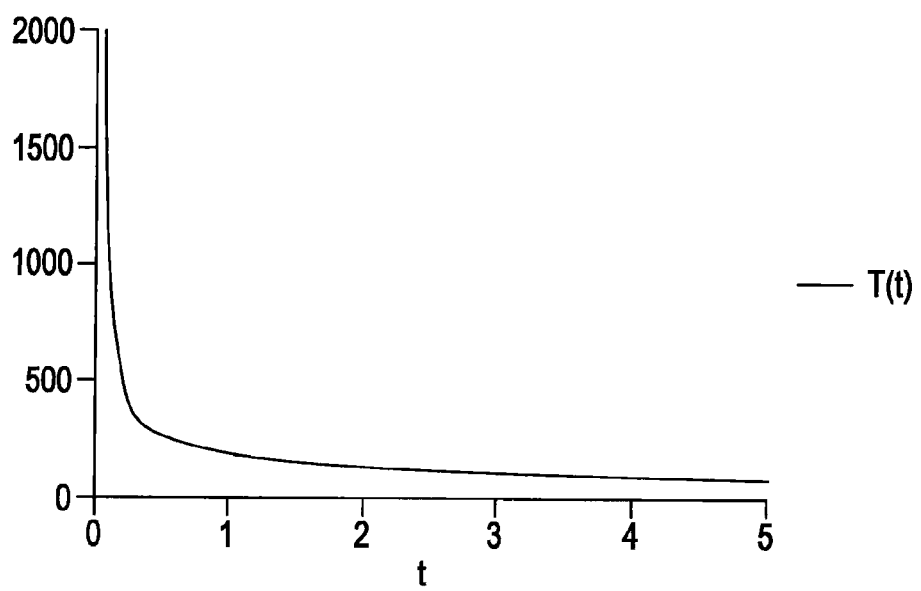
FIG. 14 shows an exponentiated form of the line representing $\log(T(t))$ in FIG. 13 in accordance with exemplary embodiments of the invention.
Figure 15:
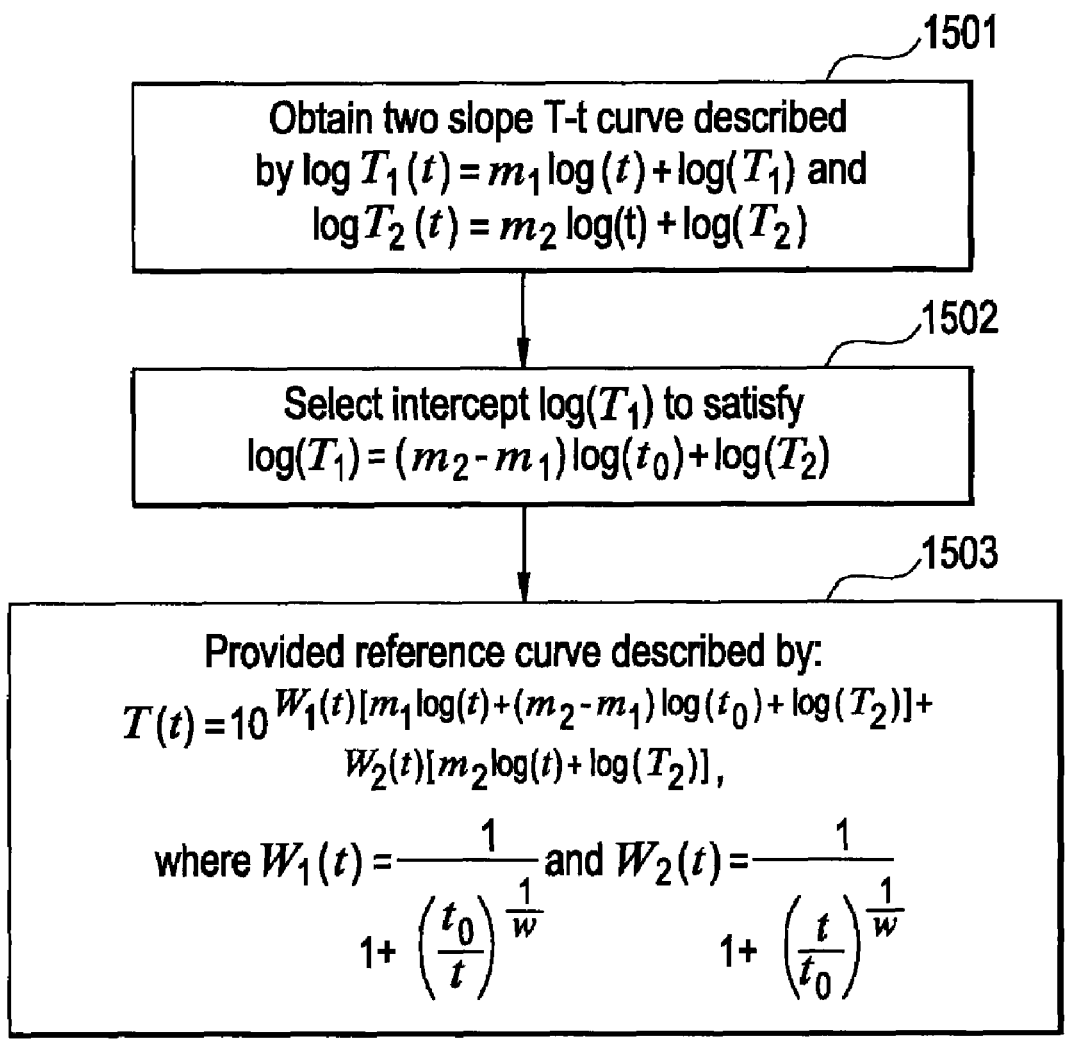
FIG. 15 is a flowchart illustrating a process of calculating a reference curve for a two slope temperature-time curve as performed by the system of FIG. 1 in accordance with exemplary embodiments of the invention.

An exponentiated form of the line representing log(T(t)) in FIG. 13 (i.e., a temperature-time curve for the dual slope function) is shown in FIG. 14. For example, a sharp, but continuous knee may occur at the junction. FIG. 15 is a flowchart illustrating a process of calculating a reference curve for a two slope temperature-time curve as performed by the system of FIG. 1 in accordance with exemplary embodiments of the invention. Blocks 1501, 1502, 1503 summarize the above described implementation with respect to FIGS. 11-14.

FIG. 16 is a flowchart illustrating a process of infrared image data acquisition and analysis that includes a two slope reference curve calculation option as performed by the system of FIG. 1 in accordance with exemplary embodiments of the invention. In that regard, FIG. 16 includes blocks 200, 201, 2203, 204, 205, 206, 207, 208, 209, 210, which were described above with respect to FIG. 2. Following block 201, a standard single slope reference curve is precalculated in block 1602 according to the implementation described above with respect to FIG. 4. Following block 204, the T-t curve is evaluated in block 1603. If the T-t curve is a single slope curve, a single slope reference curve is calculated for the T-t curve in block 1604 according to the implementation described above with respect to FIG. 4. If the T-t curve is a two slope curve, a two slope reference curve is calculated for the T-t curve in block 1605 according to the implementation described above with respect to FIGS. 5-15.

Thus, the technical effect of exemplary embodiments of the invention is an adjustment of temperature-time (T-t) reference curves, used in thermal imaging, for adaptation to deep flaw detection in anisotropic media, which includes that two lines of variable slope can be joined at an adjustable point in time so that the slope is continuous at the junction. Furthermore, the technical effect of exemplary embodiments of the invention is a nondestructive testing method and apparatus for determining and displaying the actual thickness of an object through the use of high speed infrared (IR) transient thermography.

This written description uses examples to disclose the invention, including the best mode, and also to enable practice of the invention, including making and using any devices or systems and performing any incorporated methods. The patentable scope of the invention is defined by the claims, and may include other examples. Such other examples are intended to be within the scope of the claims if they have structural elements that do not differ from the literal language of the claims, or if they include equivalent structural elements with insubstantial differences from the literal languages of the claims.

What is claimed is:

1. A method for executing a computer readable program on a computer, the method comprising:
   receiving a first line, described by $y_1(x)=m_1 x+B_1$, and a second line, described by $y_2(x)=m_2 x+B_2$, to be joined at a junction location to provide a reference curve, where $m_1$ is the slope of the first line, $B_1$ is the y-intercept of the first line, $m_2$ is the slope of the second line, and $B_2$ is the y-intercept of the second line;
   selecting the y-intercept, $B_1$, to satisfy $B_1=(m_2-m_1)x_0+B_2$;
   calculating the reference curve representing the first line and the second line joined at the junction location according to $y(x)=Y_1(x)+Y_2(x)$, where $$Y_1(x) = W_1 y_1(x),\ Y_2(x) = W_2 y_2(x),\ W_1(x) = \frac{1}{1+e^{\frac{(x_0-x)\log 10}{w}}},$$

$$W_2(x) = \frac{1}{1+e^{\frac{(x-x_0)\log 10}{w}}},$$

x is a variable location on the x-axis, $x_0$ is the junction location, w is a width parameter controlling the junction sharpness, and $W_1+W_2=1$; and
   outputting the reference curve for storage or display.

2. The method of claim 1, wherein:
   the first line and the second line represent a two slope log-log temperature-time curve of an anisotropic material described respectively by $\log T_1(t)=m_1 \log(t)+\log(T_1)$ and $\log T_2(t)=m_2 \log(t)+\log(T_2)$, where $x=\log(t)$, $B_1=\log(T_1)$, and $B_2=\log(T_2)$; and
   the reference curve is used in thermal imaging for adaptation to deep flaw detection in the anisotropic material and is described by $\log T(t)=W_1(t)[m_1 \log(t)+(m_2-m_1)\log(t_0)+\log(T_2)]+W_2(t)[m_2 \log(t)+\log(T_2)]$, where $$W_1(t) = \frac{1}{1+\left(\frac{t_0}{t}\right)^{\frac{1}{w}}}\ \text{and}\ W_2(t) = \frac{1}{1+\left(\frac{t}{t_0}\right)^{\frac{1}{w}}}.$$

3. The method of claim 2, wherein the reference curve is described in the temperature-time space by $T(t)=10^{W_1(t)[m_1 \log(t)+(m_2-m_1)\log(t_0)+\log(T_2)]+W_2(t)[m_2 \log(t)+\log(T_2)]}$.

4. The method of claim 3, wherein the reference curve is described in the temperature-time space by $T(t)=T_2 t_0^{(m_2-m_1)W_1(t)} t^{m_1 W_1(t)+m_2 W_2(t)}$.

5. An image processing computer system having a computer readable program configured to:
   receive a first line, described by $y_1(x)=m_1 x+B_1$, and a second line, described by $y_2(x)=m_2 x+B_2$, to be joined at a junction location to provide a reference curve, where $m_1$ is the slope of the first line, $B_1$ is the y-intercept of the first line, $m_2$ is the slope of the second line, and $B_2$ is the y-intercept of the second line;
   select the y-intercept, $B_1$, to satisfy $B_1=(m_2-m_1)x_0+B_2$; and
   calculate the reference curve representing the first line and the second line joined at the junction location according to $y(x)=Y_1(x)+Y_2(x)$, where $$Y_1(x) = W_1 y_1(x),\ Y_2(x) = W_2 y_2(x),\ W_1(x) = \frac{1}{1+e^{\frac{(x_0-x)\log 10}{w}}},$$

$$W_2(x) = \frac{1}{1+e^{\frac{(x-x_0)\log 10}{w}}},$$

x is a variable location on the x-axis, $x_0$ is the junction location, w is a width parameter controlling the junction sharpness, and $W_1+W_2=1$, wherein the reference curve is output for storage or display.

6. The system of claim 5, wherein:
   the first line and the second line represent a two slope log-log temperature-time curve of an anisotropic material described respectively by $\log T_1(t)=m_1 \log(t)+\log(T_1)$ and $\log T_2(t)=m_2 \log(t)+\log(T_2)$, where $x=\log(t)$, $B_1=\log(T_1)$, and $B_2=\log(T_2)$; and the reference curve is used in thermal imaging for adaptation to deep flaw detection in the anisotropic material and is described by $\log T(t) = W_1(t)[m_1 \log(t) + (m_2 - m_1) \log(t_0) + \log(T_2)] + W_2(t)[m_2 \log(t) + \log(T_2)]$, where $$W_1(t) = \frac{1}{1 + \left(\frac{t_0}{t}\right)^{\frac{1}{w}}} \text{ and } W_2(t) = \frac{1}{1 + \left(\frac{t}{t_0}\right)^{\frac{1}{w}}}.$$

7. The system of claim 6, wherein the reference curve is described in the temperature-time space by $T(t) = 10^{W_1(t)[m_1 \log(t) + (m_2 - m_1)\log(t_0) + \log(T_2)] + W_2(t)[m_2 \log(t) + \log(T_2)]}$.

8. The system of claim 7, wherein the reference curve is described in the temperature-time space by $T(t) = T_2 t_0^{(m_2 - m_1)W_1(t)} t^{m_1 W_1(t) + m_2 W_2(t)}$.

9. A computer program product, comprising a non-transitory computer usable medium having a computer readable program, wherein the computer readable program, when executed on a computer, causes the computer to:

receive a first line, described by $y_1(x) = m_1 x + B_1$, and a second line, described by $y_2(x) = m_2 x + B_2$, to be joined at a junction location to provide a reference curve, where $m_1$ is the slope of the first line, $B_1$ is the y-intercept of the first line, $m_2$ is the slope of the second line, and $B_2$ is the y-intercept of the second line;

select the y-intercept, $B_1$, to satisfy $B_1 = (m_2 - m_1)x_0 + B_2$; and calculate the reference curve representing the first line and the second line joined at the junction location according to $y(x) = Y_1(x) + Y_2(x)$, where $$Y_1(x) = W_1 y_1(x), Y_2(x) = W_2 y_2(x), W_1(x) = \frac{1}{1 + e^{\frac{(x_0 - x)\log 10}{w}}},$$

$$W_2(x) = \frac{1}{1 + e^{\frac{(x - x_0)\log 10}{w}}},$$

x is a variable location on the x-axis, $x_0$ is the junction location, w is a width parameter controlling the junction sharpness, and $W_1 + W_2 = 1$, wherein the reference curve is output for storage or display.

10. The computer program product of claim 9, wherein:

the first line and the second line represent a two slope log-log temperature-time curve of an anisotropic material described respectively by $\log T_1(t) = m_1 \log(t) + \log(T_1)$ and $\log T_2(t) = m_2 \log(t) + \log(T_2)$, where $x = \log(t)$, $B_1 = \log(T_1)$, and $B_2 = \log(T_2)$; and the reference curve is used in thermal imaging for adaptation to deep flaw detection in the anisotropic material and is described by $\log T(t) = W_1(t)[m_1 \log(t) + (m_2 - m_1) \log(t_0) + \log(T_2)] + W_2(t)[m_2 \log(t) + \log(T_2)]$, where $$W_1(t) = \frac{1}{1 + \left(\frac{t_0}{t}\right)^{\frac{1}{w}}} \text{ and } W_2(t) = \frac{1}{1 + \left(\frac{t}{t_0}\right)^{\frac{1}{w}}}.$$

11. The computer program product of claim 10, wherein the reference curve is described in the temperature-time space by $T(t) = 10^{W_1(t)[m_1 \log(t) + (m_2 - m_1)\log(t_0) + \log(T_2)] + W_2(t)[m_2 \log(t) + \log(T_2)]}$.

12. The computer program product of claim 11, wherein the reference curve is described in the temperature-time space by $T(t) = T_2 t_0^{(m_2 - m_1)W_1(t)} t^{m_1 W_1(t) + m_2 W_2(t)}$.

* * * * *

UNITED STATES PATENT AND TRADEMARK OFFICE
CERTIFICATE OF CORRECTION

PATENT NO. : 7,805,251 B2
APPLICATION NO. : 12/246896
DATED : September 28, 2010
INVENTOR(S) : Ringermacher et al.

It is certified that error appears in the above-identified patent and that said Letters Patent is hereby corrected as shown below:

In Column 7, Lines 59-60, delete "determined" and insert -- determined. --, therefor.

In Column 9, Line 56, in Equation (5), delete "$y_1(x)=m_1x+B_1y_2(x)=m_2x+B_2$" and insert -- $y_1(x)=m_1x+B_1, y_2(x)=m_2x+B_2$ --, therefor.

In Column 10, Line 4, in Equation (7), delete "$y(x)=Y_1(x)+Y_2(x)Y_1(x)=W_1y_1(x)Y_2(x)=W_2y_2(x)$" and insert -- $y(x)=Y_1(x)+Y_2(x), Y_1(x)=W_1y_1(x), Y_2(x)=W_2y_2(x)$ --, therefor.

In Column 10, Line 33, in Equation (8), delete "$x=\log(t)\ x_o=\log(t_0)\ B_2=\log(T_2)\ B_1=\log(T_1)$" and insert -- $x=\log(t), x_o=\log(t_0), B_2=\log(T_2), B_1=\log(T_1)$ --, therefor.

In Column 10, Lines 42-43, in Equation (10), delete

" $T(t)=10^{W_1(t)[m_1 \log(t)+(m_2-m_1)\log(t_0)+\log(T_2)]+W_2(t)[m_2 \log(t)+\log(T^{2)}]}$ "

and insert

-- $T(t)=10^{W_1(t)[m_1 \log(t)+(m_2-m_1)\log(t_0)+\log(T_2)]+W_2(t)[m_2 \log(t)+\log(T_2)]}$ --, therefor.

In Column 10, Line 47, in Equation (11), delete

" $T(t)=T_2 t_0^{(m2-m1)W1(t)} t^{m1 W1(t)+m2 W2(t)}$ "

and insert

-- $T(t)=T_2 t_0^{(m_2-m_1)W_1(t)} t^{m_1 W_1(t)+m_2 W_2(t)}$ --, therefor.

In Column 11, Line 17, delete "2203," and insert -- 203, --, therefor.

Signed and Sealed this
Twelfth Day of July, 2011

David J. Kappos
*Director of the United States Patent and Trademark Office*

CERTIFICATE OF CORRECTION (continued)
U.S. Pat. No. 7,805,251 B2

In Column 14, Lines 31-32, delete

" $T(t) = 10^{W_1(t)[m_1 \log(t)+(m_2-m_1)\log(t_0)+\log(T_2)]+W_2(t)[m_2 \log(t)+\log(T_2)]}$ ,"

and insert

-- $T(t) = 10^{W_1(t)[m_1 \log(t)+(m_2-m_1)\log(t_0)+\log(T_2)]+W_2(t)[m_2 \log(t)+\log(T_2)]}$ --, therefor.